United States Patent [19]
Potter

[11] 3,957,807
[45] May 18, 1976

[54] PROCESS FOR MANUFACTURE OF BIPYRIDYLS

[75] Inventor: Sheila Antoinette Potter, Runcorn, England

[73] Assignee: Imperial Chemical Industries Limited, London, England

[22] Filed: July 9, 1975

[21] Appl. No.: 594,551

Related U.S. Application Data

[62] Division of Ser. No. 379,308, July 16, 1973, which is a division of Ser. No. 171,349, Aug. 12, 1971, Pat. No. 3,787,427.

[30] Foreign Application Priority Data

Aug. 17, 1970 United Kingdom............... 39481/70

[52] U.S. Cl............................................. 260/296 D

[51] Int. Cl.$^2$...................................... C07D 213/22
[58] Field of Search................................ 260/296 D

[56] References Cited
UNITED STATES PATENTS

| | | | |
|---|---|---|---|
| 2,962,502 | 11/1960 | Hiliary et al. | 260/296 D |
| 3,040,052 | 6/1962 | Jubb | 260/296 D |
| 3,189,610 | 6/1965 | Widnes | 260/296 D |

Primary Examiner—Alan L. Rotman
Attorney, Agent, or Firm—Cushman, Darby & Cushman

[57] ABSTRACT

A process for the manufacture of bipyridyls which comprises heating a pyridine with a 4-halopyridine at a temperature of at least 150°C.

10 Claims, No Drawings

PROCESS FOR MANUFACTURE OF BIPYRIDYLS

This is a division of application Ser. No. 379,308, filed on July 16, 1973, which is, in turn, a division of application Ser. No. 171,349, filed on Aug. 12, 1971, and now U.S. Pat. No. 3,787,427, issued on Jan. 22, 1974.

This invention relates to the manufacture of heterocyclic bases and particularly to a process for the manufacture of bipyridyls, notably 4,4'-bipyridyls and 2,2'-bipyridyls.

According to the present invention we provide a process for the manufacture of bipyridyls which comprises heating a pyridine with a halogen, a 4-halopyridine or a 1-(4-pyridyl)-pyridinium halide at a temperature of at least 150°C.

The 4-substituted pyridine (i.e. the 4-halopyridine or the 1-(4-pyridyl)-pyridinium halide), which may contain substituents for example one or more alkyl groups in addition to the 4-substituent and which may be in the form of its hydrohalide, is preferably employed in a substantially anhydrous condition. The pyridine with which the halogen or the 4-substituted pyridine is heated may be pyridine itself or a substituted pyridine, for example an alkyl substituted pyridine in which the 4-position is unsubstituted. Mixtures of a pyridine and water may be employed although such mixtures tend to result in reduced yields of bipyridyls so that a substantially anhydrous pyridine is preferred.

The temperature at which the mixture of the pyridine and the halogen or 4-substituted pyridine is heated is advantageously at least 180°C although there is no advantage in employing a temperature greater than 400°C. The preferred temperature range is 180°C to 300°C. Usually the reaction will be carried out in a sealed vessel, for example a Carius tube, so that superatmospheric conditions are created when the mixture is heated. The mixture may be heated in the presence or absence of oxygen.

The products of the process are generally mixtures of isomeric bipyridyls, notably 4,4'-bipyridyls and 2,2'-bipyridyls, although we have found that the reaction conditions and notably the temperature at which and the time for which the mixture is heated can be selected to yield a product consisting essentially of a single bipyridyl species. We have found that in general at the lower temperatures in the range, for example about 180°C, the product is essentially 4,4'-bipyridyl with traces only of other isomers, irrespective of the time of reaction. At higher temperatures, for example about 300°C the initial product is again predominantly 4,4'-bipyridyl but increasing the time for which the mixture is heated leads to the production of a mixture of isomeric bipyridyls and eventually to a product which contains 2,2'-bipyridyl as the major constituent. Thus, for example, if a mixture of 1-(4-pyridyl)-pyridinium chloride and excess pyridine is heated at 300°C the product after 4 hours consists essentially of 4,4'-bipyridyl whereas the product after 10 hours consists of a mixture of 2,2'-bipyridyl, 2,4'-bipyridyl and 4,4'-bipyridyls wherein the 2,2'-bipyridyl is by far the major product. Moreover if the mixture is heated at 300°C for 10 hours in the presence of an alkali-metal halide, for example potassium iodide, the product consists essentially of 2,2'-bipyridyl and at most only traces of 4,4'-bipyridyl are obtained. Thus the reaction can be carried out to yield 4,4'-bipyridyl or 2,2'-bipyridyl substantially free from other isomeric bipyridyls.

The 4-substituted pyridines for use in the process of the invention can be produced in a variety of ways. For example 1-(4-pyridyl)-pyridinium chloride can be produced by reaction of pyridine or an alkyl pyridine with thionyl chloride at room temperature in known manner; this reaction is rapid and exothermic and is accompanied by a rise in temperature of the reaction mixture but it is not generally necessary to employ cooling means to maintain the temperature at about room temperature. Alternatively 1-(4-pyridyl)-pyridinium halides can be produced in known manner by reacting pyridine or an alkyl pyridine with a halide, especially a chloride, of a metal of variable valency wherein the metal is in a higher valency state, for example tungsten hexachloride, niobium pentachloride and tantalum pentachloride. The pyridine may be heated with the metal halide at a temperature of up to 120°C if necessary. It is not always necessary to isolate the pyridyl pyridinium chloride from the reaction mixture. However, we have found that higher conversions of the pyridyl pyridinium salt are obtained if it is separated prior to the conversion from any sulphur liberated during the reaction.

4-substituted pyridines for use in the process may also be obtained by the reaction of pyridine or an alkyl pyridine with a halide of a metal of the B-sub Groups of Groups III to V of the Periodic Table according to Mandeleoff, for example silicon tetrachloride, tin tetrachloride, antimony pentachloride and thallium trichloride. It is not necessary to isolate the 4-substituted pyridine from the reaction mixture.

A still further process for producing 4-substituted pyridines comprises reacting pyridine with a halogen at temperatures up to 150°C in known manner. At temperatures below 50°C, for example at room temperature, it may be necessary to carry out the reaction in the presence of a Friedel Crafts' catalyst for example aluminium trichloride or ferric chloride. The resulting 1-(4-pyridyl)-pyridinium salt may be converted to bipyridyls without isolation from the reaction mixture. Indeed the pyridine and the halogen may be heated initially at a temperature of greater than 150°C so that bipyridyls are obtained directly and this technique is a preferred embodiment of the invention. In this embodiment it is believed that a 4-substituted pyridine as hereinbefore defined may be formed as an intermediate species but the mechanism of the reaction is not fully understood and the invention is in no way limited by any particular theory.

The reaction between the pyridine and the halogen may be carried out by heating a solution of the halogen in the pyridine. We have found that in general reaction of the pyridine and the halogen is favoured by temperatures in excess of 200°C, for example about 300°C and that at these higher temperatures the product tends to contain mixed isomers, of which 2,2'-bipyridyls are the major constituents. However, at lower temperatures, for example about 180°C, the product contains a 4,4'-bipyridyl as the major constituent. Moreover, if a pyridine and bromine are heated in the presence of palladium bromide, the product is essentially the 2,2'-bipyridyl, irrespective of time and temperature.

The bipyridyls can be isolated from the reaction mixture in which they are formed by conventional methods, for example by adding an aqueous solution of a base, notably sodium hydroxide, followed by solvent extraction of the resulting basic mixture using for example a hydrocarbon solvent, especially toluene. The isomeric bipyridyls can be identified by gas/liquid chromatography and they may be separated by thin layer chromatography.

The bipyridyls are useful for conversion by quaternisation for example by means of an alkyl halide into N,N'-disubstituted-bipyridylium salts which are useful herbicides.

The invention is illustrated but in no way limited by the following examples wherein yields of products are based on 4-substituted pyridine fed unless otherwise stated.

EXAMPLES 1–14

These examples demonstrate the conversion of 1-(4-pyridyl)-pyridinium chloride to 4,4'-bipyridyl and/or 2,2'-bipyridyl.

The experimental procedure in each case was as follows: 1-(4-pyridyl)-pyridinium chloride (1g) or its hydrochloride (1g) as shown in Table I and pyridine and in some examples a metal salt were mixed together in a Carius tube which was then evacuated and sealed. The mixture was then heated at the temperature and for the period of time shown in Table I, after which it was cooled to room temperature and analysed. The products are shown in Table I, in which PPC represents 1-(4-pyridyl)-pyridinium chloride and PPC.HCl its hydrochloride.

EXAMPLES 15–25

These examples demonstrate the conversion of 4-halopyridines to bipyridyls.

The experimental procedure was the same as described in Example 1–14 but using a 4-halopyridine instead of pyridyl pyridinium chloride.

Table I

| Example | PPC or PPC.HCl | mls pyridine | metal or metal salt (g) | Temp (°C) | Time (hrs) | Products % |
|---|---|---|---|---|---|---|
|  |  |  |  |  |  | Bipyridyls |
| 1 | PPC | 1 | — | 300 | 10 | 2,2'- (25)<br>4,4'- (13)<br>2,4'- (1.2) |
| 2 | PPC.HCl | 6 | — | 180 | * | 4,4'- (17.4)<br>2,4'- (<1) |
| 3 | PPC.HCl | 10 | — | 180 | 4 | 4,4'- (11.3) |
| 4 | PPC | 6 | — | 180 | 4 | 4,4'- (11.8) |
| 5 | PPC.HCl (ultra-pure) | 6 | — | 180 | 4 | 4,4'- (15.3) |
| 6 | PPC | 6 | — | 250 | 4 | 4,4'-(15) |
| 7 | PPC | 6 mls of aqueous pyridine ($H_2O$=30%) | — | 180 | 4 | 4,4'- (7.75) |
| 8 | PPC.HCl | 6 mls of aqueous pyridine (30% $H_2O$) | — | 180 | 4 | 4,4'- (6.15) |
| 9 | PPC | 6 | — | 120 | 10 | No bipyridyls |
| 10 | PPC | 7 | $FeSO_4$ (1.44) | 180 | 4 | 4,4'- (5.6) |
| 11 | PPC | 7 | CaCl (0.51) | 180 | 4 | 4,4'-(4.8) |
| 12 | PPC | 7 | KI (0.85) | 300 | 10 | 2,2'- (17.5)<br>(No 4,4'-) |
| 13 | PPC | 7 | Za (0.2) | 180 | 4 | 4,4'- (6) |
| 14 | PPC | 7 mls of aqueous pyridine (30% $H_2O$) | 2a (0.2) | 180 | 4 | 4,4'- (5) |

Table II

| Ex. No. | Substituted Pyridine | Mls Pyridine | Temp (°C) | Time (Hrs) | Products (%) |
|---|---|---|---|---|---|
| 15 | 4-bromopyridine.HCl | 5 | 250 | 4 | 4,4'- (44.5) |
| 16 | 4-bromopyridine.HCl | 6 | 180 | 4 | 4,4'- (61.5) |
| 17 | 4-bromopyridine.HCl | 3.5g | 180 | 5 | 4,4'- (10) |
| 18 | 4-chloropyridine.HCl | 6 | 160 | 4 | 4,4'- (26) |
| 19 | 4-bromopyridine.HCl | 6 | 160 | 4 | 4,4'- (26.7) |
| 20 | 4-bromopyridine | 6 | 180 | 4 | 4,4'- (46.5) |
| 21 | 4-bromopyridine.HCl | 6 | 180 | 4 | 4,4'- (62) |
| 22 | 4-bromopyridine.HCl | 2.5 | 300 | 4 | (2,2'- (15)<br>(2,4'- (24)<br>(4,4'-(21) |
| 23 | 4-chloropyridine.HCl | 6 | 180 | 4 | 4,4'- (54) |
| 24 | 4-bromopyridine.HCl | 6 | 90 | 5 | (PPC (63)<br>(No bipyridyls) |
| 25 | 4-bromopyridine.HCl | 6 | 60 | 2 | PPC (17.3) |

* pyridine.HCl used instead of pyridine.

EXAMPLES 26–46

These examples illustrate the production of 4,4'-bipyridyls and 2,2'-bipyridyls from pyridine and halogen.

The experimental procedure was as follows, details of amounts of reagents, temperature and time being shown in Table III, in which "Products (%)" indicates the yield of bipyridyl based on halogen fed.

A. Halogen = Chlorine

A solution of chlorine in pyridine was prepared by passing chlorine in a stream of nitrogen through pyridine at a temperature of 0°C. A portion of the solution was transferred under an atmosphere of nitrogen to a Carius tube which was then sealed and heated to the required temperature at which it was maintained for the desired period of time.

The tube was then cooled to room temperature and its content filtered. The solid was dissolved in a mixture of methanol and aqueous ammonia and the resulting solution was analysed by gas/liquid chromatography.

B. Halogen = Bromine or Iodine

Pyridine was placed in a Carius tube and its temperature was reduced to 0°C. The halogen was slowly added in the required amount and then the Carius tube was frozen, evacuated, sealed and then heated at the desired temperature for the required period of time. The reaction mixture was treated and analysed as described above.

Table III

| Example | Mls Pyridine | Halogen | Metal Halide (%) | Temp (°C) | Time (Hrs) | Products (%) |
|---|---|---|---|---|---|---|
| 26 | 7 | Br$_2$(0.4 ml) | — | 180 | 4 | 4,4'- (21) |
| 27 | 7 | Br$_2$(0.4 ml) | — | 180 | 2 | 4,4'- (9.7) |
| 28 | 6 | Br$_2$(2 ml) | — | 180 | 3 | 4,4'- (2.4) |
| 29 | 7 | Cl$_2$(0.19g) | — | 300 | 10 | 2,2'- (29) 2,4'- (2) 4,4'- (1) |
| 30 | 7 | Cl$_2$(0.19g) | — | 300 | 10 | 2,2'- (75) 4,4'- (1) |
| 31 | 7 | Br$_2$(0.4 ml) | — | 300 | 10 | 4,4'- (22) 2,2'- (20) 2,4'- (6.4) |
| *32 | 6 | Br$_2$(0.4 ml) | — | 180 | 4 | 4,4'- (10.6) |
| 33 | 7 | I$_2$(1.7g) | — | 300 | 2 | 2,2'- (10.7) 2,4'- (2) |
| 34 | 6 | Br$_2$(0.4 ml) | PdBr$_2$(1g) | 300 | 2 | 2,2'- (17.4) 2,4'- (1.6) 4,4'- (0.8) |
| 35 | 7 | Br$_2$(0.4 ml) | PdBr$_2$(1g) | 300 | 10 | 2,2'- (62.5) 2,4'- (10) 4,4'- (6.7) |
| 36 | 6 | Br$_2$(0.4 ml) | PdBr$_2$(1g) | 120 | 4 | No Bipyridyls |
| 37 | 7 | Br$_2$(0.4 ml) | Na$_2$PdCl$_6$(1g) | 300 | 10 | 2,2'- (43.5) 2,4'- (7.8) 4,4'- (Trace) |
| 38 | 7 | Br$_2$(0.4 ml) | PdBr$_2$(1g) Na$_2$PdCl$_6$(1g) | 300 | 4 | 2,2'- (6.4) 2,4'- (2.5) |
| 39 | 7 | Br$_2$(0.4 ml) | CuBr$_2$(0.1g) | 300 | 10 | 2,2'- (22) 4,4'- (19) 2,4'- (8.6) |
| 40 | 6 | Br$_2$(0.4 ml) | CuBr$_2$(0.1g) | 150 | 16 | 4,4'- (22.6) 2,2'- (Trace) |
| 41 | 6 | Br$_2$(0.4 ml) | CuBr$_2$(1g) | 150 | 16 | 4,4'- (11.8) 2,2'- (Trace) |
| 42 | 7 | Br$_2$(0.4 ml) | CuBr$_2$(0.1g) | 300 | 10 | 4,4'- (22) 2,2'- (20) 2,4'- (6.4) |
| *43 | 6 | Br$_2$(0.4 ml) | — | 180 | 4 | 4,4'- (10.6) |
| **44 | 7 | | NaCl (1g) | 300 | 10 | 2,2'- (6) 2,4'- (Traces) |
| **45 | 7 | | FeCl$_3$ (1g) | 300 | 10 | 2,2'- (13.6) 2,4'- (6.0) 4,4'- (Trace) |
| **46 | 7 | | CuCl$_2$ (1g) | 300 | 10 | 2,2'- (11.6) 2,4'- (8.6) 4,4'- (4.3) |

*in the presence of pyridine.HCl (1g)
**a solution of chlorine in pyridine was employed

EXAMPLES 47–68

Pyridine (14 ml) was placed in a Carius tube and its temperature was reduced to 0°C. Bromine (0.8 ml) was added slowly in the desired amount and where appropriate (see Table below) a metal salt also was added. The contents of the tube were frozen and the tube was then evacuated and sealed. The contents of the tube were then heated at the temperature and for the time shown in the Table below. The resulting mixture was cooled to room temperature and filtered and the solid residue was dissolved in a mixture of methanol and aqueous ammonia. The resulting solution was analysed for bipyridyls by gas/liquid chromatography.

Table IV

| Example | Additive | Temp (°C) | Time (Hrs) | Pyridine Consumed (%) | Yield 4,6'-bipyridyl on Pyridine | Yield 4,6'-bipyridyl on Bromine |
|---|---|---|---|---|---|---|
| 47 | — | 180 | 4 | 14 | 39 | 33 |
| 48 | — | 200 | 4 | 20 | 44 | 52 |
| 49 | AlCl₃ (1g) | 220 | 4 | 13 | 60 | 47 |
| 50 | — | 220 | 4 | 10 | 87 | 52 |
| 51 | — | 240 | 4 | 21 | 38 | 46 |
| 52 | — | 180 | 4 | 20 | 16 | 19 |
| 53 | — | 260 | 4 | 18 | 42 | 46 |
| 54 | — | 220 | 4 | 14 | 48 | 38 |
| 55 | — | 220 | 4 | 13 | 70 | 52 |
| 56 | — | 220 | 4 | 15 | 52 | 45 |
| 57 | CuBr₂ (0.2g) | 220 | 4 | 14 | 61 | 52 |
| 58 | — | 220 | 10 | 15 | 63 | 53 |
| 59 | — | 220 | 4 | 32 | 55 | 52 |
| 60 | AlCl₃ (0.3g) | 220 | 4 | 35 | 24 | 50 |
| 61 | — | 220 | 4 | 21 | 88 | 56 |
| *62 | — | 220 | 4 | 52 | 34 | 35 |
| **63 | C₆H₆ (7 ml) | 220 | 4 | 35 | 34 | 35 |
| 64 | — | 220 | 4 | 18 | 42 | 45 |
| 65 | — | 220 | 4 | 10 | 50 | 59 |
| ***66 | — | 220 | 4 | 27 | 49 | 40 |
| 67 | — | 220 | 2 | 24 | 24 | 35 |
| 68 | — | 220 | 1 | 14 | 34 | 28 |

*amount bromine increased to 2.4 ml
**amount pyridine reduced to 7 ml
***amount bromine increased to 1.6 ml

I claim:

1. A process for the manufacture of a 2,2'-bipyridyl, a 2,4'-bipyridyl or a 4,4'-bipyridyl which consists essentially of heating pyridine in the liquid phase under substantially anhydrous conditions with a member selected from the group consisting of a 4-halopyridine and the hydrohalide addition salts thereof at a temperature of at least 150°C and up to 400°C.

2. A process as claimed in claim 1 wherein the 4-halopyridine is 4-bromopyridine.

3. A process as claimed in claim 1 wherein the 4-halopyridine is 4-chloropyridine.

4. A process as claimed in claim 1 wherein the temperature is from 180°C to 300°C.

5. A process as claimed in claim 1 which is carried out under superatmospheric pressure.

6. A process as claimed in claim 5 which is carried out in a sealed vessel.

7. A process as claimed in claim 1 wherein the temperature is at least 200°C.

8. A process as claimed in claim 1 wherein the pyridine and the 4-halopyridine are heated in the presence of an alkali-metal halide.

9. A process as claimed in claim 8 wherein the alkali-metal halide, is potassium iodide.

10. A process as claimed in claim 1 wherein the hydrochloride is employed.

* * * * *